US010039922B2

(12) United States Patent
Régnier (10) Patent No.: US 10,039,922 B2
(45) Date of Patent: Aug. 7, 2018

(54) ACTIVE IMPLANTABLE MEDICAL DEVICE COMPRISING A CONNECTOR-FREE CAPSULE, PERMANENTLY CONNECTED TO A MICROLEAD

(71) Applicant: SORIN CRM SAS, Clamart (FR)

(72) Inventor: Willy Régnier, Longjumeau (FR)

(73) Assignee: Sorin CRM SAS, Clamart (FR)

( * ) Notice: Subject to any disclaimer, the term of this patent is extended or adjusted under 35 U.S.C. 154(b) by 126 days.

(21) Appl. No.: 15/073,295

(22) Filed: Mar. 17, 2016

(65) Prior Publication Data
US 2016/0271404 A1   Sep. 22, 2016

(30) Foreign Application Priority Data

Mar. 18, 2015   (FR) ..................................... 15 52211

(51) Int. Cl.
| | |
|---|---|
| A61N 1/375 | (2006.01) |
| A61N 1/362 | (2006.01) |
| A61N 1/05 | (2006.01) |
| A61B 5/042 | (2006.01) |
| A61B 5/00 | (2006.01) |

(52) U.S. Cl.
CPC .......... *A61N 1/3754* (2013.01); *A61B 5/0422* (2013.01); *A61B 5/686* (2013.01); *A61N 1/056* (2013.01); *A61N 1/362* (2013.01); *A61N 1/3752* (2013.01); *A61N 1/3756* (2013.01)

(58) Field of Classification Search
None
See application file for complete search history.

(56) References Cited

U.S. PATENT DOCUMENTS

| | | | |
|---|---|---|---|
| 7,899,554 B2 * | 3/2011 | Williams | ............... A61N 1/057 |
| | | | 607/126 |
| 8,311,633 B2 * | 11/2012 | Ransbury | ................. A61F 2/95 |
| | | | 607/36 |

(Continued)

FOREIGN PATENT DOCUMENTS

WO   WO-2013/080038   6/2013

OTHER PUBLICATIONS

Preliminary Search Report for French Patent Application No. 1552211, dated Dec. 8, 2015, 2 pages.

*Primary Examiner* — Brian T Gedeon
(74) *Attorney, Agent, or Firm* — Foley & Lardner LLP (57) ABSTRACT

The device comprises a sealed body housing electronic circuits, and extending from said body, a microlead comprising microcables connected to remote electrodes. The device has no connector between the microlead and the electronic circuits. Each microcable is permanently connected to its pole by connection means. The connection means comprises an insulating base hermetically crossed by feedthrough pins, a support for the base, conductive connection parts each comprising a first passage for a microcable and a second passage for a feedthrough pin, an insulating guiding and holding part mounted on the support and locked thereon. The guiding and holding part having cavities for the connection parts, each cavity opening in its bottom on a passage wherein a pin projects. The device also includes a transition and protection element encapsulating the guiding and holding part, the connection parts and the adjoining regions of the microcables.

18 Claims, 6 Drawing Sheets

(56) References Cited

U.S. PATENT DOCUMENTS

| | | | |
|---|---|---|---|
| 8,554,336 B2* | 10/2013 | Bly | A61N 1/056 |
| | | | 607/116 |
| 8,644,934 B2* | 2/2014 | Hastings | A61N 1/372 |
| | | | 607/32 |
| 8,705,599 B2* | 4/2014 | dal Molin | A61N 1/37288 |
| | | | 375/219 |
| 9,248,271 B2* | 2/2016 | Regnier | A61N 1/05 |
| 9,265,864 B2* | 2/2016 | Regnier | A61N 1/056 |
| 9,623,234 B2* | 4/2017 | Anderson | A61N 1/056 |
| 2003/0114905 A1* | 6/2003 | Kuzma | A61N 1/0551 |
| | | | 607/116 |
| 2007/0123949 A1* | 5/2007 | Dabney | A61N 1/3754 |
| | | | 607/37 |
| 2010/0137960 A1 | 6/2010 | Moffitt et al. | |
| 2010/0305629 A1* | 12/2010 | Lund | A61N 1/378 |
| | | | 607/2 |
| 2012/0109258 A1* | 5/2012 | Cinbis | A61B 5/0028 |
| | | | 607/60 |
| 2013/0110127 A1 | 5/2013 | Bornzin et al. | |
| 2013/0123875 A1 | 5/2013 | Varady et al. | |
| 2015/0217123 A1* | 8/2015 | Deterre | A61N 1/3785 |
| | | | 607/7 |
| 2017/0189681 A1* | 7/2017 | Anderson | A61N 1/3684 |

* cited by examiner

ACTIVE IMPLANTABLE MEDICAL DEVICE COMPRISING A CONNECTOR-FREE CAPSULE, PERMANENTLY CONNECTED TO A MICROLEAD

CROSS-REFERENCE TO RELATED PATENT APPLICATIONS

This application claims the benefit of and priority to French Patent Application No. 1552211 filed on Mar. 18, 2015, which is incorporated herein by reference in its entirety.

FIELD

The present disclosure generally relates to "active implantable medical devices" as defined by Directive 90/385/EEC of 20 Jun. 1990 of the Council of the European Communities, including implantable devices that continuously monitor heart rhythm and deliver to the heart, if necessary, electrical stimulation, resynchronization and/or defibrillation pulses in case of arrhythmia detected by the device.

The present disclosure mainly describes a cardiac detection/stimulation system, however, it should be understood, that the present disclosure may also be applied, mutatis mutandis, to the detection/stimulation of other organs such as nervous system (including brain stimulation or nerve stimulation), arterial or lymphatic system, gastrointestinal system (stomach, intestine) or the respiratory system.

BACKGROUND

A non-limiting example of such a system and corresponding therapy described in the present disclosure relates to patients with heart failure (HF), to which the implantation of a cardiac resynchronization device such as a CRT-P (pacemaker) or a CRT-D (pacemaker further provided with a defibrillator function) is proposed.

The therapy may aim to synchronize the contraction of both ventricles, and if necessary, those of the ventricles relative to the atrium in order to improve the patient's condition by optimizing the different phases of the hemodynamic cycle. The devices may implement a technique called "CRT" (Cardiac Resynchronization Therapy) or "BVP" (Bi-Ventricular Pacing) by issuing, as necessary, electrical pulses ensuring joint and permanent stimulation of both, left and right, ventricles to resynchronize the contractions of the latter.

The implantable device may include an endocardial pacing lead that is implanted in the right ventricle, and, for the stimulation of the left ventricle, a lead may be inserted into the coronary venous system via the coronary sinus, so as to place the stimulation electrode of the lead against the wall of the left ventricle. Alternatively, an epicardial lead may be introduced into the pericardial sac and secured to the outer wall of the heart muscle at the left ventricle. The device may also comprise a third lead positioned in the right atrial cavity, and may be used for detection of the contraction of the atrium in order to synchronize the stimulation of the ventricles in accordance with the chronology of the atrioventricular delay.

These endocardial or coronary leads may be introduced through the patient's venous system, which can create complications such as displacement, insulation or conductor breakdown, fibrosis development, etc.

To reduce these risks, a new generation of devices has been developed, which are in the form of implantable autonomous capsules for placement in a heart chamber (ventricle, atrium, or even arterial left heart chamber), and are usually designated as "leadless capsules". These capsules are devoid of any physical connection to a main implantable device (such as the housing of a stimulation pulse generator) or non-implantable device (external device such as programmer or monitoring device for remote monitoring of the patient).

For this reason, they are referred to as "leadless" capsules, to distinguish them from electrodes disposed at the distal end of a conventional lead, traversed over its entire length by one or more conductors galvanically connecting the distal electrode to a connector located at the opposite, proximal end of the lead, said connector being intended to be connected to the housing of the pulse generator.

The WO2013/080038 A2 describes an example of such an endocardial or epicardial leadless capsule, and of its means of communication with the outside environment. The device also includes a pulse generator implanted subcutaneously, with a wired connection to an endocardial or epicardial electrode placed at a detection/stimulation site. The synchronization of the system is ensured by a wireless connection between the leadless capsules and the remote master generator.

The leadless capsules may replace the conventional endocardial leads, such as the right ventricular leads and/or the right atrial leads, or the epicardial leads, but because of the dimensions of the capsules, they may not be suitable substitutes for leads that pace the left ventricle, which are introduced into the coronary venous system. The left ventricular pacing leads may be needed for detection/stimulation of the left ventricle, and for the application of a CRT therapy.

In addition, the endocardial arterial network (providing access to the left cavities) remains at risk, even with a leadless capsule, because of the serious risk of bleeding or of blood clots, which can form arterial emboli.

On the other hand, as regards the left coronary leads, the need to use a guidewire for implantation, the standard for the multipolar left lead connectors (IS-4 or DF-4 standards) and the need for a central lumen formed in the lead body for introduction of the guide wire, are constraints that limit the ability to reduce the diameter of the coronary leads and therefore to reach new target areas for stimulation of the left ventricle that remain difficult to reach today.

Here the term "hybrid capsule" may be understood as including a device for the detection/stimulation of the left ventricle, comprising:

A body, which can be of the same shape and in the same configuration as a leadless capsule, with a low power consumption electronic architecture, a miniaturized power source and wireless communication means for communication with other capsules or external devices, The body may include a lead directly extending from the body of the capsule without continuity solution (e.g., without intermediate connector or interface) so as to form an integral and fully autonomous device, The lead may be a "Microlead", that is to say a miniaturized lead of very small diameter (typically not more than 1 French, or 0.33 mm) and free of an internal lumen, formed of a conductive core cable coated with an insulating layer, and a distal region of the cable includes one or more selectively exposed areas forming detection/stimulation electrodes.

SUMMARY

An object of the present disclosure is to provide, between the lead and the capsule body in such a device, a mechanical and electrical connection that is robust, compact and reliable.

In an exemplary embodiment of the present disclosure, an active implantable medical device may be an autonomous hybrid capsule comprising a sealed body housing electronic circuitry and power supply means for the electronic circuitry and, extending from said body, at least one detection and/or therapy delivery lead, this lead having a plurality of microcables each formed of an electrically conductive core cable connected to a respective pole of said electronic circuitry and at least one electrode for detection and/or therapy delivery.

In some embodiments, the lead may be a microlead having a set of microcables, wherein the device may have no electrical connection between the microlead and the electronic circuits, each microcable being connected to its respective pole by permanent connection means, and the permanent connection means may comprise:

An insulating base hermetically crossed by a plurality of pins corresponding to the respective poles of the electronic circuits;

A support hermetically carrying the base;

A set of conductive connection parts, each connection part comprising a first passage for a respective core of a microcable and a second passage for a respective feedthrough pin and being welded to the latter;

An insulating guiding and retaining part mounted on the support and mechanically locked thereto, said guiding and retaining part having a plurality of cavities for the respective connection parts, each cavity opening at its bottom on a passage in which a respective feedthrough pin is projecting; and At least one transition and protection element encapsulating the guiding and retaining part the connection parts and the regions of the microcables which are adjoining.

According to various exemplary embodiments:

The support may be part of the body of the capsule;

The support may include a part forming a front face whereby the connection means are fixed to the body of the capsule;

The guiding and retaining part may be mounted on the support by a translation movement followed by a rotational movement ensuring the engagement of locking tabs respectively provided on the guiding and retaining part and on the support and;

In some embodiments, at least some tabs may form a ramp (slight incline) providing a pressurization of the tabs therebetween upon rotation. The guiding and retaining part may comprise a main body carrying locking tabs and guiding said part in the support, and a narrower second body to the periphery of which the recesses are formed;

The connection parts may each comprise a main body in which a passage for the respective feedthrough pin is formed, and an appendix extending laterally from said passage for the pin and wherein a passage for the core of the microcable is formed;

The transition and protection element may comprise a region of flexible material ensuring the encapsulation and whose cross-section gradually decreases from the body of the capsule to the microlead;

The transition element may include, around the proximal region of the microlead attached to the body of the capsule, a transition region of variable stiffness gradient, decreasing in the distal direction;

The transition region may be formed of at least one separate part of the encapsulation region and comprises at its proximal end a locking arrangement in the encapsulation region;

The body of the capsule may have a generally elongate shape with substantially constant cross section, and the connection means may be provided at one end of the body and occupy a cross-section at most equal to that of the body.

DRAWINGS

Further features, characteristics and advantages of the present disclosure will become apparent to a person of ordinary skill in the art from the following detailed description of preferred embodiments, made with reference to the drawings annexed, in which like reference characters refer to like elements and in which.

DETAILED DESCRIPTION

We will now describe an exemplary embodiment, applied to a system such as a cardiac resynchronizer (CRT).

As explained in the introduction, this example is only illustrative, and various embodiments of the present disclosure may be implemented in the context of different detection/stimulation configurations, including in a context that is not necessarily linked to cardiac diagnosis and/or therapy.

Figure 1:
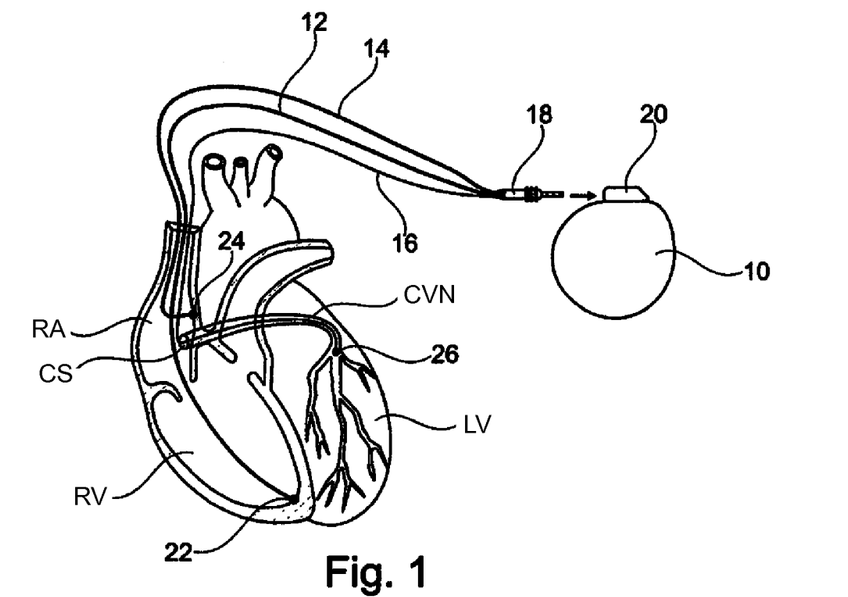
FIG. 1 shows, in implantation situation, the various elements constituting a CRT system according to the prior art.

FIG. 1 shows, in a position of implantation, the various elements of a CRT system according to the prior art.

In some embodiments, the system may include a CRT pacemaker generator 10, for example from the Paradym CRT family from Sorin CRM, Clamart, France.

The generator 10 may include a housing of a volume of 30 cm³ to which three leads 12, 14 and 16 are coupled by means of a connector 18 inserted into a connector head 20 of the generator 10, typically a connector of the IS-4 standard type. The generator 10 includes a long longevity battery as the power supply of the internal circuits for control and detection/stimulation, the average power consumption of which is on the order of 30 μW.

The leads of the CRT system may comprise an endocardial right ventricular lead 12 introduced into the venous system, having a lead body of a typical diameter of 4 French (1.33 mm), and terminated at its distal end by a lead head carrying a detection/stimulation electrode 22 anchored in the cavity of the right ventricle RV.

The system may also (optionally) comprise an endocardial right atrial lead 14 the structure of which is comparable to that of the lead 12 with a lead body terminated at its distal end by a lead head implanted in the right atrium RA and provided with an atrial detection electrode 24.

For detection/stimulation of the left ventricle, it is not possible, or at least extremely risky to use an endocardial lead, and for this reason, a lead inserted into the coronary venous system CVS, via the coronary sinus CS opening into the right ventricle, is generally used as a left ventricular lead 16.

The coronary lead 16 may include, at its distal end, an electrode 26 positioned against the wall of the left ventricle LV so as to stimulate the latter in the area of this electrode. Alternatively, the left ventricular lead 16 may be an epicardial lead introduced between the wall of the myocardium and the epicardial bag surrounding the latter, so as to come in contact with the outer wall of the ventricular muscle to be stimulated.

Figure 2:
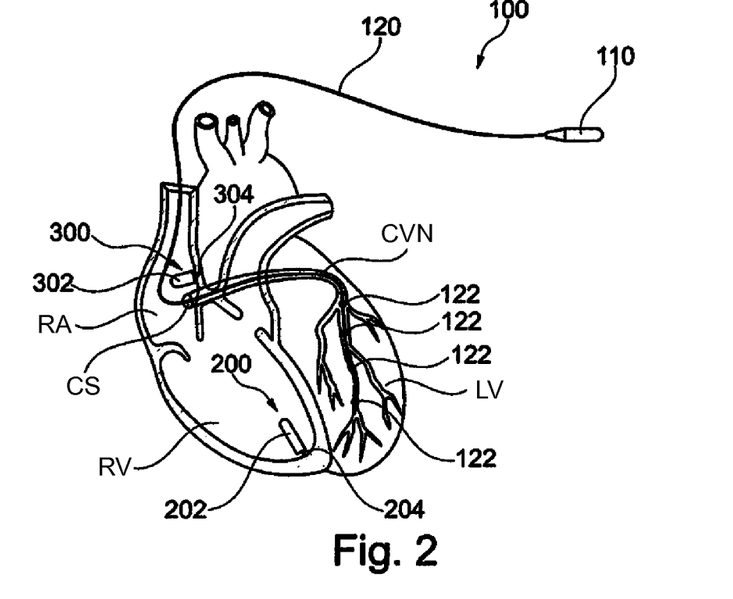
FIG. 2 shows, in implantation situation, the various elements constituting a CRT system.

FIG. 2 is a CRT system 100 according to an exemplary embodiment of the present disclosure.

The system comprises, instead of the generator 10, a device hereinafter called "hybrid capsule" 100, associated with a single lead 120 coupled to the body 110 of the hybrid capsule by a simplified permanent connection system, replacing the connector such as the IS-4 connector 18 of the system according to the prior art shown in FIG. 1. In other words, the lead 120 seamlessly extends from the body 110 of the capsule due to the absence of a connector.

The lead 120 may be a "microlead" lead, as described in particular in EP 2719422 A1 (Sorin CRM), herein incorporated by reference in its entirety. The lead 120 may have a very small diameter in its distal part, such as a diameter less than 1.5 French (0.5 mm), and more preferably, a diameter of 1 French (0.33 mm) or less.

The lead 120 may be made from at least one microcable consisting of an electrically conductive core coated with an insulating layer surrounding the core and having at least one selectively exposed zone formed in the insulation layer to form a detection/stimulation electrode. Various microcable structures are described in EP 2581107 A1 (Sorin CRM), which is herein incorporated by reference in its entirety, and may be referred to for further details.

As described in EP 2719422 A1 cited above, a plurality of such microcables are assembled together into a strand of microcables, each being electrically independent, so as to obtain a multipolar microlead with a plurality of separately selectable electrodes 122.

The multipolar microlead allows the implementation of a function called "electrical repositioning" which consists of selecting, among a number of points corresponding to a plurality of stimulation electrodes connected respectively to one of the microcables of the lead, the point, or combination of points, providing the highest efficiency. This selection can be made at the time of implantation of the lead and/or later, by performing tests at regular intervals to ensure that the originally or currently selected site is optimal, and selecting a different site otherwise.

The active distal part of the microlead 120 is implanted in the coronary venous network CVN so that the electrodes 122 are in contact with different areas of the wall of the left ventricle LV. The various electrodes 122 may constitute a plurality of exposed areas of a monopolar zones (these electrodes being thus all active and electrically connected in parallel), or by different, selectively switchable, electrodes of a multipolar microlead.

The system may further comprise a leadless capsule 200 implanted in the right ventricle RV. The capsule 200 is of the leadless type such that it lacks a physical connection to an implantable main device (such as the generator 10 of FIG. 1) or an external device. The capsule 200 comprises a leadless body 202 with an anchoring member 204 at one of its ends, usually a protruding helical screw which axially extends from the body 202 of the capsule 200, and is intended to penetrate and screw into the cardiac tissue at the implantation site, in the same manner as conventional screw leads.

EP 2394695 A1 (Sorin CRM), herein incorporated by reference in its entirety, describes a leadless capsule with an anchoring screw, and an accessory allowing its implantation at the chosen site by docking the axial screw end of the capsule against the implantation site, driving the capsule in rotation to attach it to permanently in the heart wall wherein it is maintained by the axial anchoring screw, and then removing the accessory, the capsule remaining attached to the heart wall at the implantation site.

The body 202 of such a leadless capsule is usually in a generally cylindrical shape with a length of 20 to 40 mm, an outer diameter of less than 6 mm (two French, a size imposed by the size of the access path through the peripheral venous network), and a volume of about 1 cm³.

The leadless capsule may include a low power electronic architecture, typically 5 to 8 μW, which allows powering by an energy harvesting system (described for example in EP 2638930 A1 (Sorin CRM) or EP 2639845 A1 (Sorin CRM), both of which are herein incorporated by reference in their entirety) instead of a battery with a limited lifetime.

As illustrated FIG. 2, a second leadless capsule 300 of a type similar to the capsule 200 may be anchored to the right atrium RA. The second leadless capsule includes a body 302 and means for anchoring 304 to the right atrium RA so as to collect the atrial depolarization signals.

Capsules 200 and 300 may be conventional leadless capsules of a type already known, and are not described in detail for this reason.

Figure 3:
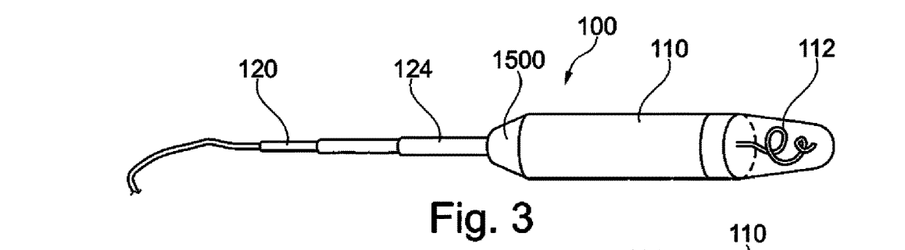
FIG. 3 is an enlarged view of the capsule of the hybrid assembly of FIG. 2.
Figure 4:
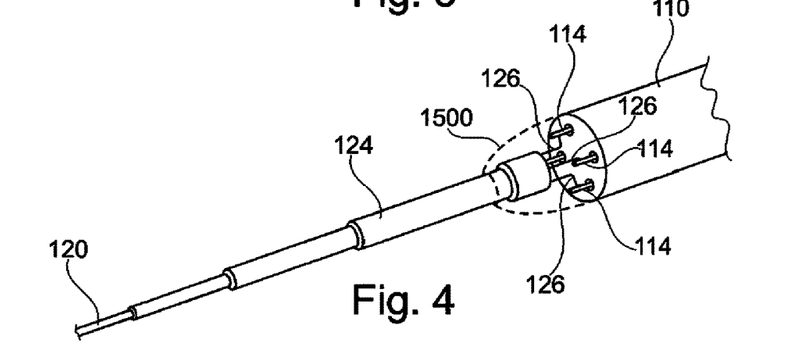
FIG. 4 is a schematic showing the the electrical connection of the conductors of the microlead to the internal circuits of the hybrid capsule.

FIGS. 3 and 4 are enlarged views showing details of the hybrid capsule 100 of the system according to an embodiment of the present disclosure.

The hybrid capsule 100 may include a waterproof, biocompatible and atraumatic tubular metal (or titanium alloy) body 110. The outer diameter of this body may be 6 mm (18 French) or less, has a length of about 40 mm or less, and a volume on the order of 1 cm³. In various embodiments, the body 110 of the hybrid capsule 100 may have substantially the same dimensions as the capsules 200 and 300.

At one end, the body 110 of the hybrid capsule 100 may include an antenna 112 for wireless communication. The antenna 112 may enable the hybrid capsule 100 to communicate with an external device, such as a programmer or a remote data transmission device, by RF telemetry in the MICS (Medical Implant Communication System) band, MEDS, in public commonplace ISM bands used by medical devices, or by communication under the Bluetooth protocols.

For HBC communication between capsules, a ring shaped electrode electrically insulated from the body 110 of the capsule and the antenna 112, may be provided to transmit data through contact with the tissues or the blood via electrical pulses in the patient's body.

At the opposite end of the body 110 from the antenna 112, the microlead 120 extends from the body 110 of the hybrid capsule 100. An intermediate transition region 124 having a length of about 30 mm is provides a gradient of progressive stiffness between the rigid end of the body 110 and the flexible portion of the microlead 120.

Referring to FIG. 4, the connection between the microcable 126 of the microlead 120 and the internal circuitry contained in the body 110 of the hybrid capsule is carried by hermetic feedthroughs 114, which are unipolar feedthroughs with a welded conductive pin on a base secured to the body 110 of the hybrid capsule and each connected to a respective microcable 126 of the microlead 120.

Figure 5:
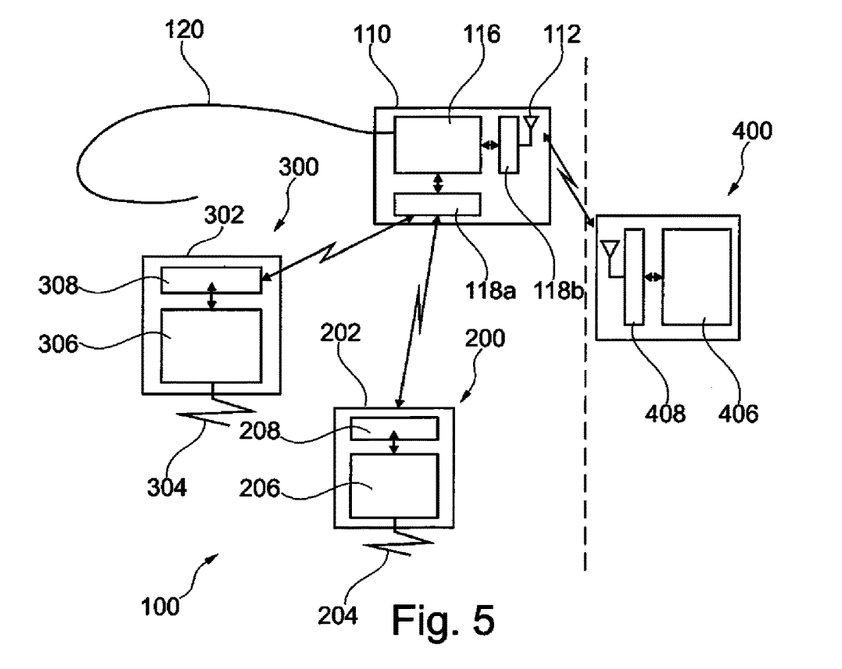
FIG. 5 is a functional diagram showing the interactions between the various elements of the system.

Referring to FIG. 5, a block diagram illustrates, according to various embodiments, the interactions between the various devices of the system introduced above.

Each of the hybrid (100) or leadless (200 and 300) capsules comprises electronic control circuits, respectively 116, 206, 306, coupled to wireless communication transmitter/receiver means, 118a-118b, 208 and 308, respectively, allowing mutual communication between the different capsules 100, 200, 300 as well as communication of the hybrid capsule 110 with a remote device 400. The remote device 400 includes control circuits 406 coupled to transmitter/receiver means 408. The remote device 400 may include the programmer used by a practitioner, communication then being used to interrogate the implantable system, to read the data stored in memory, to change settings, etc., or a home monitoring device for home monitoring of the patient's status, with the possibility of transmitting information to a remote site, such as a hospital or other remote monitoring facility.

We will now describe in detail, with reference to FIGS. 6-13, the connection between the microcables 126 of the microlead 120 and the internal circuitry of the hybrid capsule through the feedthroughs 114.

Figure 6:
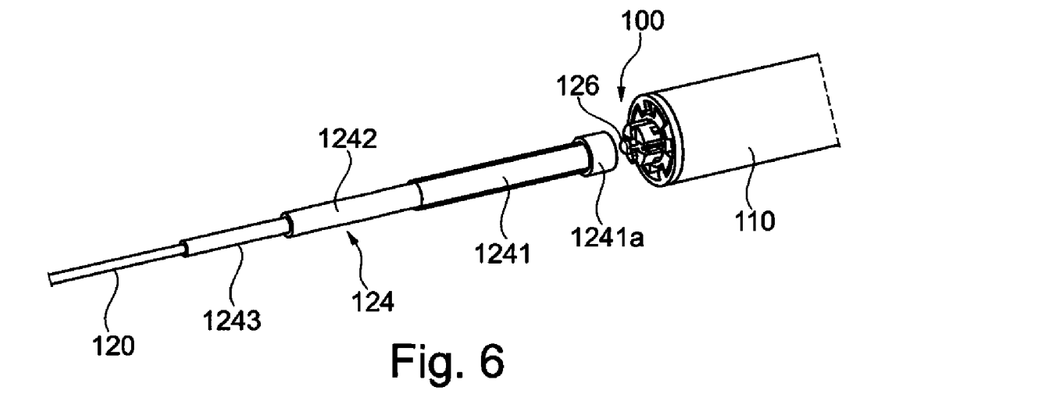
FIG. 6 is an exploded perspective view of a portion of the components of the connection between the hybrid capsule and the microlead.

The connection uses a first part 1100 forming the front face of the body 110 of the hybrid capsule and a connecting support part 1200 which supports the functions of positioning, holding and locking of components involved in the connection.

The first part 1100 forming the front face includes a planar disc shaped base portion 1120 for axial support against the front end of the capsule. The base portion 1120 is traversed by a central opening 1122 for securing a base 1300 illustrated in FIGS. 10 and 11 and which will be described hereinafter. The base portion 1120 is extended axially by an annular peripheral flange 1110 from which a set of locking tabs 1130 (here four in number are illustrated, however more or less may be used) intended to cooperate with corresponding locking members of the connecting support part 1200.

Figure 7:
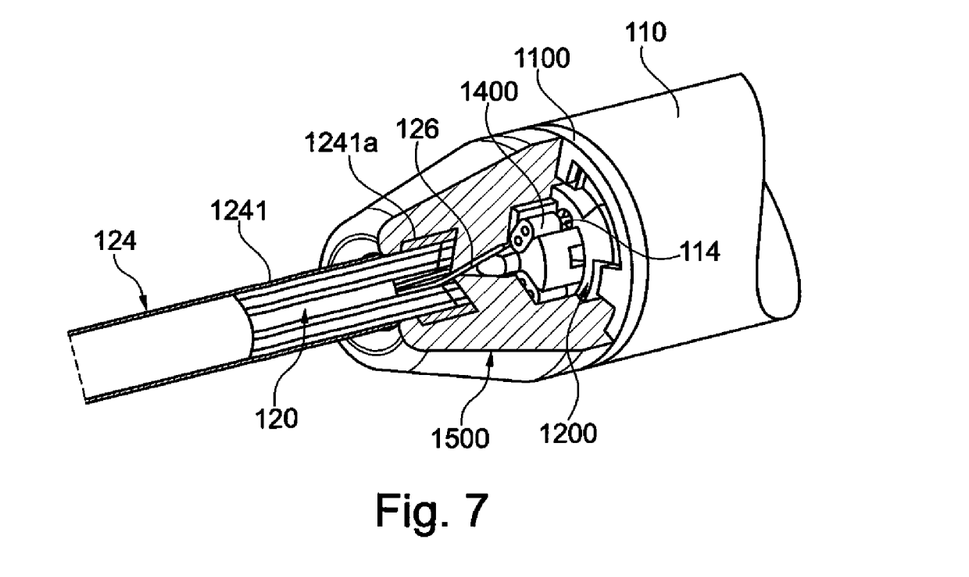
FIG. 7 is a partial perspective view of said connection.

As shown in FIG. 7, the first part 1100 forming the front face has dimensions that correspond to the transverse dimensions of the hybrid capsule so as not to increase the size of the capsule.

The connecting support part 1200 includes a main body 1210 of a generally circular cross section from which four sectors 1220 extend outwards. From each sector a locking tab 1230 extends in a circumferential direction and only on part of its thickness.

Figure 8:
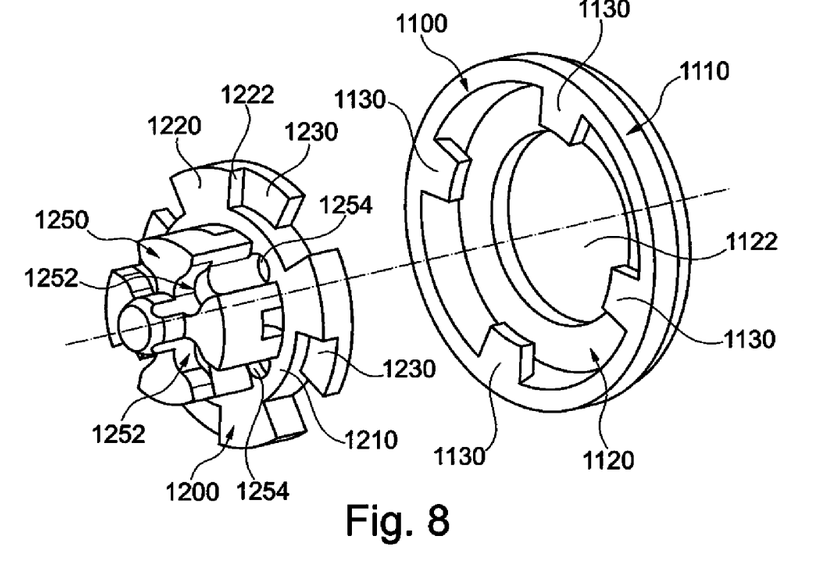
FIG. 8 is an exploded perspective view of two components of said connection.

The tabs 1230 are adapted to cooperate with the tabs 1130 of the first part 1100 forming the front face, a bayonet mounting principle, the connecting support part 1200 being engaged by axial translation in the cavity defined by the flange 1110 of the first part 1100 so that the sectors 1220 provided with their respective locking tabs 1230 pass between two adjacent tabs 1130, then rotated through a determined angle around the main axis of the capsule, clockwise in FIG. 8, so that the locking tabs 1230 of the connecting support part 1200 are locked behind the tabs 1130 of the first part 1100, firmly holding the two parts secured to one another.

The firmness of this locking can be achieved by giving tabs 1130 and/or 1230, at their surfaces which come into mutual contact, a slope of a few degrees, for example, 3°, a gradual clamping being obtained with a progressive pressurizing of the tabs between them, up to the maximum rotation defined by the abutment of each tab 1130 against the shoulder 1222 existing between the corresponding tab 1230 and the sector 1220 which carries it.

The connecting support part 1200 also includes a superstructure formed by a sub-body 1250, of a generally cylindrical contour, coaxial with the main body 1210 but of smaller diameter. This secondary body houses four generally cylindrical cavities 1252 distributed at its periphery and whose forms are generally complementary to those of four respective connection parts 1400, associated with microcables 126, as will describe later. These cavities 1252 extend into and through openings 1254 crossing through the main body 1210 (to the right in FIG. 8 for example).

The connecting support part 1200 ends, at the sub-body 1250 side, with an axial protrusion 1260 providing a preguiding of the connection parts 1400.

The first part 1100 may be made of an electrically insulating and biocompatible material, such as polyetheretherketone (PEEK) or a thermoplastic elastomer of polyurethane such as Tecothane or Pellethane (registered trademarks).

The connecting support part 1200 may be made of, for example, titanium alloy, so as to be laser welded to the body 110 of the hybrid capsule, which may also be made of titanium.

Figure 9:
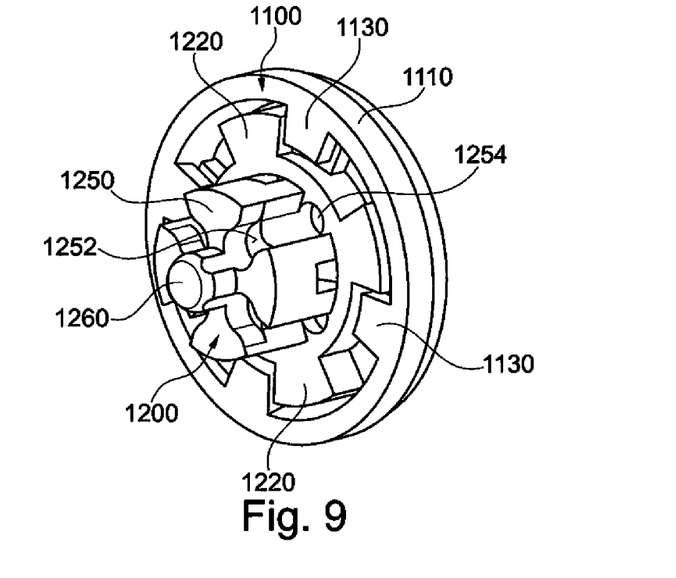
FIG. 9 is a perspective view of the two components in an assembled state.

The configuration described above provides an extremely compact assembly between the parts 1100 and 1200, both in terms of diameter (equal to that of the capsule and typically 5 to 7 mm) and axial length (typically 3 to 4 mm).

Figure 10:
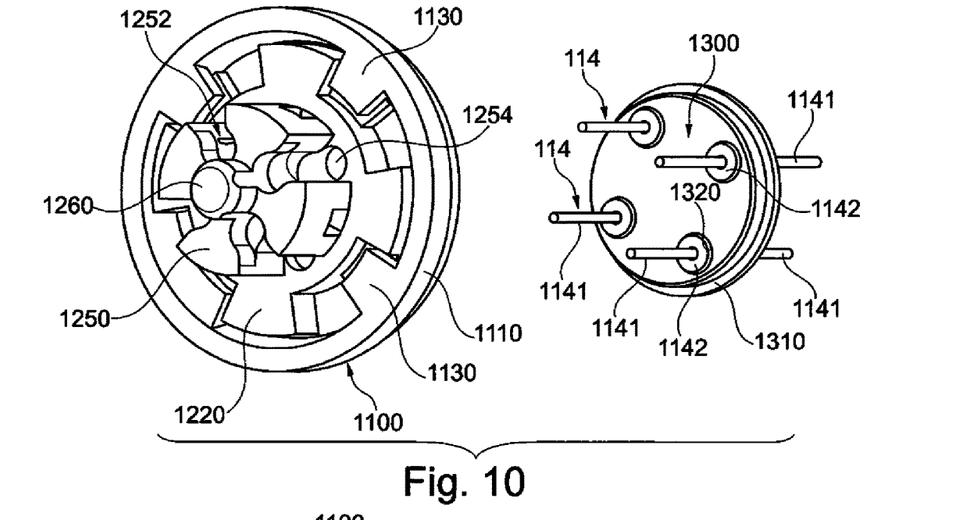
FIG. 10 is an exploded perspective view of the assembly of FIG. 9 and of a third component of the connection.
Figure 11:
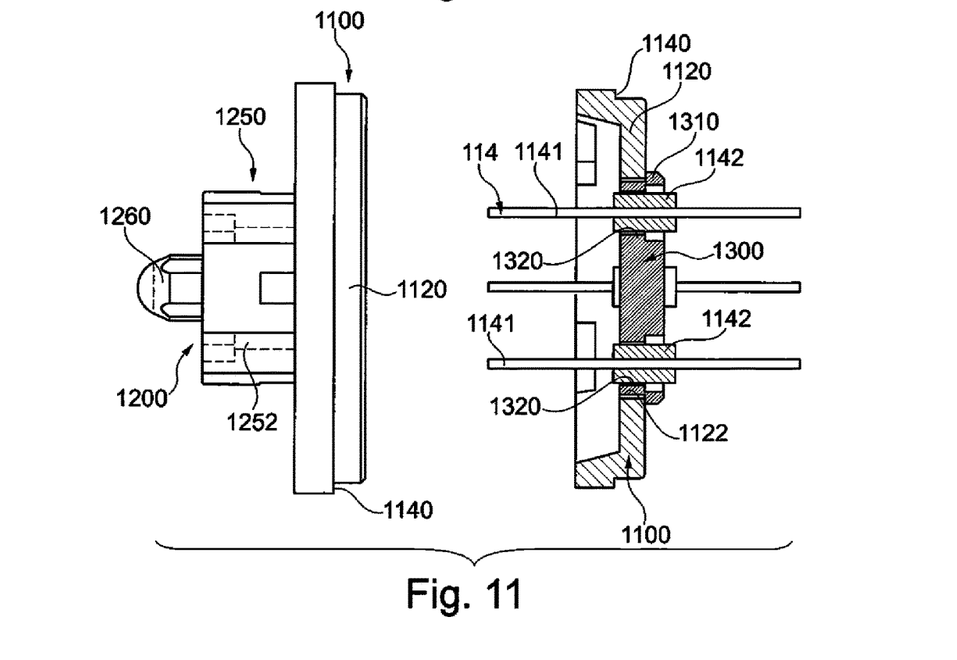
FIG. 11 is an axial sectional view of the third component of the connection and also shows the assembly of FIG. 9 in side elevation view.

As illustrated in FIGS. 10 and 11, the sealed feedthroughs 114, ensuring the electrical connection between the microcables 126 of the microlead 120, are four unipolar feedthroughs which are mounted in the base 1300, consisting of a general disc-shaped part which is housed from the rear into the central opening 1122 of the first part 1100 forming the front face. A peripheral shoulder 1310 allows stalling the base 1300 in the axial direction.

Each feedthrough comprises an electrically conductive cylindrical pin 1141 which extends axially through an insulator 1142.

The feedthroughs (1141 pins and insulators 1142) are mounted and sealed in respective complementary recesses 1320 formed in the base. The feedthroughs may be welded by laser shots, which ensure the sealing.

In the present embodiment, the base 1300 holding the feedthroughs 114 may be welded, for example, by laser shots on the front face of the first part 1100.

Figure 12:
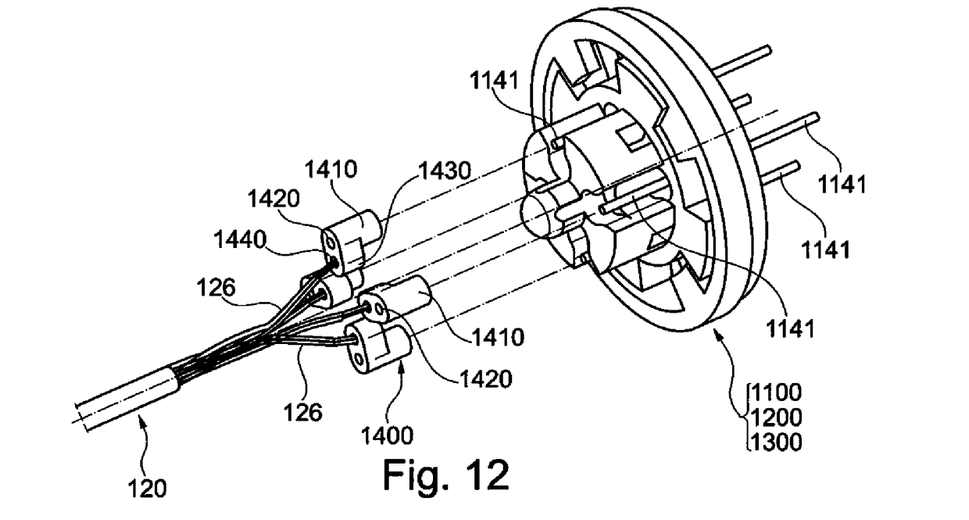
FIG. 12 is an exploded perspective view of the assembly of the three components of FIGS. 10 and 11 with the microlead and with associated connection parts.
Figure 13:
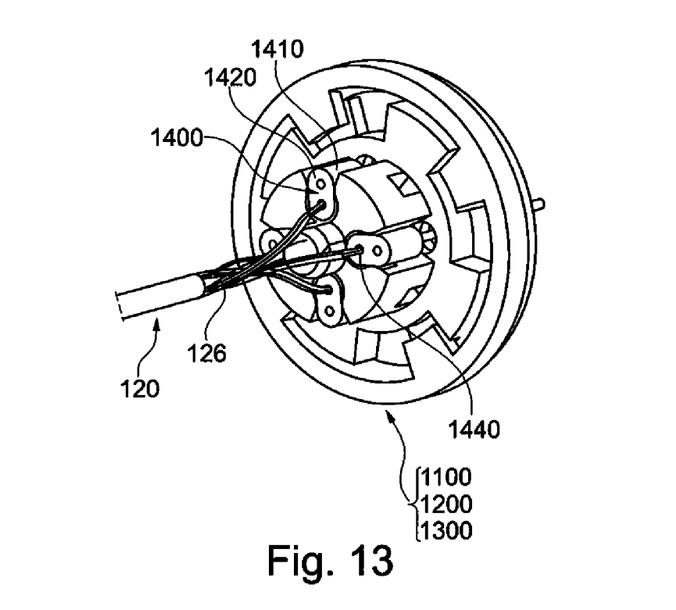
FIG. 13 is a perspective view of the assembled elements of FIG. 12.

Referring to FIGS. 12 and 13, we will now describe the manner in which the microcables 126 of the microlead 120 (here four in number) are connected to respective feedthroughs.

Each microcable 126 may comprise a conductive strand coated with an insulating sheath. Each conductive strand is exposed at the end of the strand on a length of about 1 mm and then an electrical connection part 1400, preferably made of stainless steel, is mounted on this exposed portion.

Each connection part 1400 comprises a generally cylindrical main body 1410 crossed through by an axial passage 1420 intended to accommodate the pin 1141 of a respective feedthrough 114. The cylindrical body 1410 is extended laterally over a portion of its axial length by a connection projection 1430 with the associated microcable 126. The connection projection 1430 is crossed by an axial passage 1440, the diameter of which is selected according to that of the conductive strand of the microcable 126.

The mechanical and electrical connection between the connection part 1400 and the associated microcable 126 is ensured by introducing the exposed end of the strand into the axial passage 1440 and by providing a welding laser shot, preferably at the cable end (on the right side of the Appendix 1430 in FIG. 12), so as not to damage the structure, particularly the insulating sheath.

The electrical connection between the microcables 126 and the feedthroughs 114 is finalized by engaging the connection parts 1400 on the respective pins 1141, the latter being engaged in the axial passages 1420. This operation is done by engaging the connecting parts 1400 into their respective cavities 1252 formed in the connecting support part 1200, the openings 1254 that extend these cavities being aligned with the pins 1141 and the latter projecting into said openings 1254 and said cavities 1252 from the base 1300.

Once this placement is made, a laser welding may be performed at the free ends of the pins 1141 (at the left of connection parts 1400 in FIGS. 12 and 13).

The connection parts 1400 are then locked in their respective cavities 1252, and locked according to the six degrees of freedom.

Referring to FIGS. 6 and 7, the intermediate transition portion 124 between the body 110 of the capsule 100 and the lead 120, as well as an overmolded part, will now be described.

This part may be formed of a set of flexible tubes made, for example, of silicone. Three tubes, 1241 to 1243, may be pre-assembled and glued together, or formed of a single tube, and then threaded through the distal side of the microlead 120 to the connection zone and glued to the lead. A stiffness gradient of the transition portion 124 provides a high mechanical strength in the connection zone formed by the parts 1100, 1200, 1300 and 1400, as described above, by limiting the curvatures. The mechanical strength progressively decreases in the direction of the microlead 120 to provide a deformability of the same order as that of the microlead 120.

In some embodiments, the silicone tube 1241 adjacent to the connection zone has a shoulder 1241a (e.g. made integral with the tube 1241 or consisting of a larger silicone tube portion glued to the tube 1241) to provide mechanical restraint between the transition portion 124 and the capsule thanks to an overmolded zone that will now be described with particular reference to FIG. 7.

This overmolded zone, designated by the reference numeral 1500, is preferably made of a polyurethane thermoplastic elastomer such as Tecothane (registered trademark), and may be formed by conventional molding techniques. The overmolded zone 1500 may have a generally conical revolution shape, with a wide base of a diameter equal to, or less than that of the capsule 110, and a narrower end. The narrower end may be rounded on the outside and on the inside of the conical end to be atraumatic, and may be formed over and trap the shoulder 1241a.

This overmolded zone 1500 locks into place all the connection parts described in the foregoing, including the connection parts 1400, to impart stability to the assembly and to ensure the recovery from the mechanical stresses between the body 110 of the capsule 100 and the microlead 120. In particular, the resistance to axial tensile stresses between the microlead 120 and the capsule is ensured by both the laser welds of the microcables 126 to the connection parts 1400, by laser welds of the connection parts 1400 to pins 1141, and by mechanical clamping of the parts, and by the overmolded zone 1500. The latter also ensures the locking of parts 1100 and 1200 against their reverse rotation by filling the empty spaces in the vicinity of the tabs 1130 and 1230.

The link and connection assembly described in the foregoing may be assembled according to the following steps:
1) mechanical assembly of the first part 1100 forming the front face, holding the base 1300 provided with the insulators 1142, and of the part forming the support link 1200 by axial translation and rotation, as described above, with clamping through the slopes of the tabs;
2) setting up and adjustment of the feedthroughs (pins 1141 and insulators 1142) in their respective housings 1320, then fixing by laser welding from the rear;
3) introduction of the exposed ends of the microcables 126 into respective connection parts 1400, and laser welding;
4) introduction of the connection parts 1400 on the pins 1141, then laser welding from the front;
5) implementation of the transition part 124 around the microlead 120 and gluing thereon;
6) encapsulation of the assembly by overmolding the components in the overmolding zone 1500;
7) assembly of the internal circuits to be accommodated in the body 110 of the hybrid capsule 100 and connection with the ends of the pins 1141 which protrude rear side and installation around these circuits of the capsule body case and fixing of the latter on the part forming the front face 1100, for example by a laser weld bead. A shoulder 1140 of the part 1100 shown in particular in FIG. 11 ensures the proper placement, with abutment, of the capsule body on the part 1100.

Many variations may be made to the hybrid capsule and to the connection means which have just been described. For example:
Although a cylindrical shape of revolution for the hybrid capsule and its connection device comprising the elements 1100, 1200, 1300 have been described and illustrated, other shapes are of course possible (e.g. oval, elliptical, polygonal such as square or rectangular—with then preferably rounded transitions, shapes);
The expected number of feedthroughs will be adapted to the number of input/output poles of the microlead;
A flattened rectangular section may be particularly suitable for the case wherein the hybrid capsule comprises an energy harvesting system, for example of the piezoelectric type; in this case, the feedthroughs 114 are advantageously provided in line;

The feedthroughs 114 may be directly integrated into a front face of the body of the capsule, the base 1300 then forming an integral part of this body.

What is claimed is:

1. An active implantable medical device for subcutaneous implantation, the active implantable device comprising:
   a capsule body housing electronic circuitry and power supply means for powering the electronic circuitry;
   at least one microlead extending from the capsule body, the at least one microlead comprising a set of microcables, each microcable of the set of microcables formed of an electrically conductive core and connected to a respective pole of said electronic circuitry via a permanent connection, the permanent connection comprising:
      an insulating base traversed by a plurality of feedthrough pins corresponding to the respective poles of the electronic circuits;
      a support hermetically receiving the insulating base;
      a set of conductive connection parts, each conductive connection part comprising a first passage for receiving the electrically conductive core of a respective microcable of the set of microcables and a second passage for receiving a respective feedthrough pin of the plurality of feedthrough pins;
      a guiding and retaining part mounted on the support and mechanically locked thereto, said guiding and retaining part having a plurality of recesses for the respective conductive connection parts, each recess having an opening at its bottom into which the respective feedthrough pin projects, wherein the guiding and retaining part is mounted on the support by a translation movement followed by a rotational movement ensuring the matching of locking tabs respectively provided on the guiding and retaining part and on the support; and
      at least one transition and protection element encapsulating the guiding and retaining part, the conductive connection parts, and adjoining regions of the microcables.

2. The device of claim 1, wherein the support is part of the capsule body.

3. The device of claim 1, wherein the support comprises a part forming a front face whereby the guiding and retaining part, the insulating base, the conductive connection parts, and the at least one transition and protection element are fixed to the capsule body.

4. The device of claim 1, wherein at least some of the locking tabs form a ramp providing pressurizing of the locking tabs between them during rotation.

5. The device of claim 1, wherein the guiding and retaining part includes a main body having locking tabs and guiding the guiding and retaining part into the support, and a secondary narrower body at the periphery of which the recesses are formed.

6. The device of claim 1, wherein the conductive connection parts each comprise a main body in which the second passage is formed, and an extension extending laterally with respect to the second passage wherein the first passage is formed.

7. The device of claim 1, wherein the transition and protection element comprises a region of flexible material providing encapsulation and whose cross-section gradually decreases from the capsule body of the capsule towards the at least one microlead.

8. The device of claim 1, wherein the transition and protection element includes, around a proximal region of the at least one microlead attached to the capsule body, a transition region with a variable stiffness gradient, decreasing in the distal direction.

9. The device of claim 7, wherein the transition and protection element includes, around a proximal region of the at least one microlead attached to the capsule body, a transition region with a variable stiffness gradient, decreasing in the distal direction, wherein the transition region is formed of at least one part distinct from the encapsulation region and comprises at its proximal end a locking arrangement in the encapsulation region.

10. The device of claim 1, wherein the capsule body has a generally elongated shape of substantially constant cross section, and wherein the connection means are provided at one end of the capsule body and occupy a cross-section at most equal to that of the capsule body.

11. An active implantable medical device comprising:
    a capsule body housing electronic circuitry, the electronic circuitry having a first pole and a second pole;
    a base traversed by a first feedthrough pin and a second feedthrough pin, the first pole connected to the first feedthrough pin and the second pole connected to the second feedthrough pin on a first side of the base;
    a support hermetically sealed to the base, the support having an opening through which the first feedthrough pin and the second feedthrough pin pass on a second side of the base;
    a connection support part mounted on the support, the connection support part having a first recess and a second recess corresponding to openings in the connection support part through which the first feedthrough pin and the second feedthrough pin on the second side of the base project, respectively;
    a first connection part having a first pin passage and a first microcable passage, a second connection part having a second pin passage and a second microcable passage, the first pin passage receiving the first feedthrough pin when the first connection part is inserted into the first recess, the second pin passage receiving the second feedthrough pin when the second connection part is inserted into the second recess;
    a microlead having a first microcable and a second microcable, the first microcable connected to the first microcable passage of the first connection part at a proximal end of the microlead, the second microcable connected to the second microcable passage of the second connection part at the proximal end of the microlead; and
    a protection region encapsulating the base, the support, the connection support part, the first connection part, the second connection part, and the proximal end of the microlead, wherein a cross-section of the protection region gradually decreases from the capsule body of the capsule towards the microlead.

12. The device of claim 11, further comprising a transition portion at the proximal end of the microlead with a variable stiffness gradient decreasing in the distal direction of the microlead.

13. The device of claim 12, wherein a proximal end of the transition portion is encapsulated by the protection region.

14. The device of claim 13, wherein the proximal end of the transition portion includes a locking arrangement.

15. The device of claim 14, wherein the transition portion has a first diameter greater than a diameter of the microlead and the locking arrangement has a second diameter greater than the first diameter.

16. The device of claim 11, further comprising a first electrode at the distal end of the microlead corresponding to the first microcable and a second electrode at the distal end of the microlead corresponding to the second microcable.

17. The device of claim 16, wherein the distal end of the microlead is for inserting into the coronary sinus such that the first electrode and the second electrode are positioned near a wall of a left ventricle.

18. The device of claim 11, wherein the electronic circuitry includes an energy harvesting system.

* * * * *